United States Patent [19]

Yahata

[11] Patent Number: 5,153,503

[45] Date of Patent: Oct. 6, 1992

[54] METHOD AND APPARATUS FOR MEASURING A CARRIER LIFETIME OF IV GROUP SEMICONDUCTOR

[75] Inventor: Akihiro Yahata, Yokohama, Japan

[73] Assignee: Kabushiki Kaisha Toshiba, Kawasaki, Japan

[21] Appl. No.: 674,886

[22] Filed: Mar. 26, 1991

[30] Foreign Application Priority Data

Mar. 26, 1990 [JP] Japan .................................. 2-73469

[51] Int. Cl.⁵ ............................................. G01R 31/26
[52] U.S. Cl. ........................... 324/158 D; 324/158 R; 324/73.1
[58] Field of Search ............ 324/158 R, 158 D, 73.1, 324/71.3; 356/369, 432, 433; 250/310, 311, 492.1, 492.2, 211 J; 136/490

[56] References Cited

U.S. PATENT DOCUMENTS

| | | | |
|---|---|---|---|
| 3,745,454 | 7/1973 | Nikirk et al. | 324/158 D |
| 4,211,488 | 7/1980 | Kleinhrecht | 356/369 |
| 4,273,421 | 6/1981 | Gurtler | 356/433 |
| 4,286,215 | 8/1981 | Miller | 324/158 D |
| 4,393,348 | 7/1983 | Goldstein et al. | 324/158 D |
| 4,413,181 | 11/1983 | Feuerbaum | 324/158 D |
| 4,578,641 | 3/1986 | Tiedje | 324/158 R |
| 4,581,578 | 4/1986 | Honma et al. | 324/158 D |
| 4,661,770 | 4/1987 | Von Roos | 324/158 D |
| 4,949,034 | 8/1990 | Imura et al. | 324/158 R |
| 5,025,145 | 6/1991 | Lagowski | 250/211 J |

OTHER PUBLICATIONS

J. Christen et al., Applied Physics Letters, vol. 44, Jan.-Jun., 1984, Localization Induced Electron-Hole Transition Rate Enhancement in GaAs Quantum Wells, pp. 84-86.

H. Jacobs et al., Proceedings of the IRE, Further Consideration of Bulk Lifetime measurement with a Microwave Electrodeless Technique, vol. 48, 1960, pp. 229-233.

Journal of Applied Physics; R. Z. Bachrach and O. G. Lorimore; Feb. 1972.

Journal of Applied Physics; B. Lax and S. F. Neustadter; Sep. 1954.

Proceedings of the IRE; H. Jacobs, A.P. Ramsa and F.A. Brand; Feb. 1960.

*Primary Examiner*—Vinh Nguyen
*Attorney, Agent, or Firm*—Oblon, Spivak, McClelland, Maier & Neustadt

[57] ABSTRACT

A method for measuring carrier lifetime of IV group semiconductors. The method includes the steps of irradiating pulse light, whose photon energy is larger than the bandgap of a IV group semiconductor and whose interval is sufficiently longer than the carrier lifetime of a IV group semiconductor, on a IV group semiconductor to be measured, exciting the IV group semiconductor, and generating excess carriers, obtaining a decay time of a band emission from a IV group semiconductor, and determining a carrier lifetime of the IV group semiconductor from the decay time of the band emission.

18 Claims, 2 Drawing Sheets

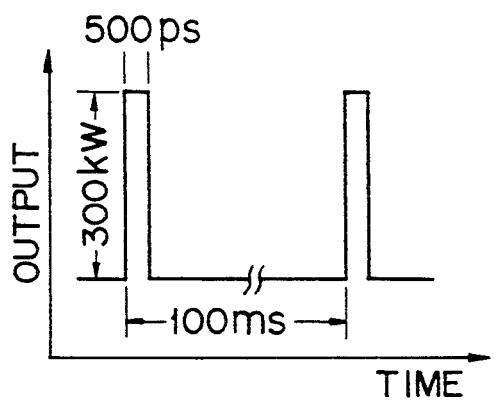
F I G. 2A
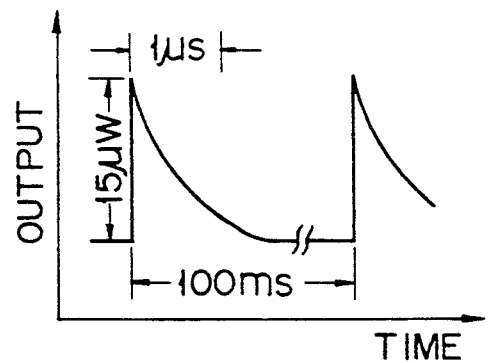
F I G. 2B
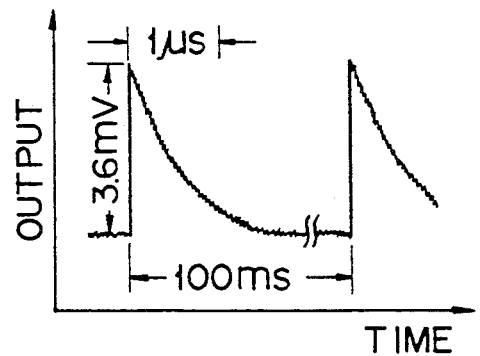
F I G. 2C
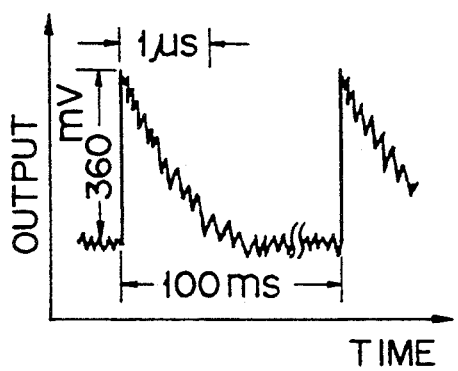
F I G. 2D
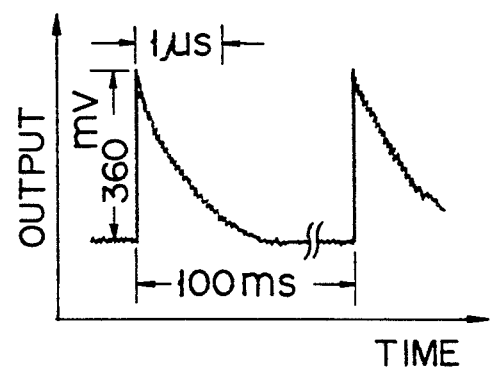
F I G. 2E

METHOD AND APPARATUS FOR MEASURING A CARRIER LIFETIME OF IV GROUP SEMICONDUCTOR

BACKGROUND OF THE INVENTION

1. Field of the Invention

The present invention relates to a method and apparatus for measuring a carrier lifetime of IV group semiconductors.

2. Description of the Related Art

It is known that carrier lifetime plays a dominant role in determining IV group semiconductor (mainly silicon) device characteristics, such as current versus voltage and switching characteristics. Therefore, many methods have been proposed to evaluate carrier lifetime. The first method among the proposed ones is photo-conductivity, which is disclosed in, for example, G. K. Wertheim and W. M. Augstyniak, Review of Scientific Instruments, vol. 27 1956, p.106. The second is reverse recovery time of a diode current, which is disclosed in, for example, B. Lax and S. F. Neustadter, Journal of Applied Physics, vol 25, 1954, p.1148. The third is open circuit voltage decay of a diode, which is disclosed in, for example, S. R. Lederhandler and L. G. Giacoletto, Proceedings of the Institute of Radio Engineering, vol. 43 1955, p.477. The fourth is microwave absorption or reflection, which is disclosed in, for example, H. Jacobs, A. P. Ramsa and F. A. Brand, Proceedings of the Institute of Radio Enginerrs, vol. 48, 1960, p.299.

However, there were many problems in the conventional carrier lifetime measuring methods for IV group semiconductors as follows:

First, it was impossible to measure carrier life-time in a minute region, for example, a region having a diameter of about 100 μm or less. Therefore, it was very difficult to know and to control the carrier life-time distribution towards vertical direction of a device (thickness direction). Secondly, it was hardly possible to measure the carrier lifetime with a wide time range of 10 ns to 1 ms. A carrier lifetime changes very much, depending on each stage of the device fabrication process and on the horizontal or vertical positions of a wafer. For example, the carrier lifetime of a raw wafer often takes a high value of about 1 ms. Whereas, the carrier lifetime of the thyristor emitter region sometimes takes a low value of 10 ns because the donor or acceptor concentrations are of the order of $10^{19}$ cm$^{-3}$. Therefore, carrier lifetime values to be able to be measured should be very wide. Thirdly, the conventional measuring methods using the electromagnetic wave, such as photo-conductivity and microwave absorption or reflection, can only be used to a wafer. Whereas, the conventional electrical measuring methods, such as reverse recovery time and open circuit voltage decay, can only be used to a diode. There are no methods which can measure the carrier lifetime of all samples from a wafer to a device. This makes it difficult to measure the carrier lifetime change during the device fabrication processes. Fourthly, carrier injection conditions are apt to be limited to a high level injection condition or a low level injection condition in the conventional measuring methods. The carrier lifetime in a high level injection condition coincides with the sum of the minority carrier lifetime and the majority carrier lifetime. Whereas, the carrier lifetime in a low level injection condition is equal to the minority carrier lifetime, which is disclosed in C. T. Sah, R. N. Noice and W. Shockley, Proc. IRE 45, 1957, p.1228. Therefore, the majority carrier lifetime can be obtained by subtracting the low level injection carrier lifetime from the high level injection carrier lifetime. However, this cannot be performed in the conventional carrier lifetime measuring methods because both injection conditions are not attained in the methods.

In the case of a compound semiconductor, such as GaAs and InP, there is another carrier lifetime measuring method besides the above-mentioned ones. A pulse light is irradiated on a compound semiconductor to excite it and to generate excess carriers in it. After the pulse light is turned off, the compound. semiconductor goes from the excited state to a thermal equilibrium state as the excess carriers decrease. A part of excess carriers disappear by emitting a band emission which originates from recombinations of electrons and holes. A carrier lifetime can be measured from the decay time of the band emission, which is disclosed in, for example, J. Christen, D. Bimberg, A. Steckenborn and G. Weimann, Applied Phys. Letters, vol. 44, 1984, p.84.

However, it was very difficult to use the above-mentioned measuring method in order to measure the carrier lifetime of IV group semiconductors from the following reasons. Since IV group semiconductors have indirect bandgaps, the band emission intensity is considerably weak. Furthermore, the peak wavelength of the band emission exists in a region where the sensitivity of a photo-detector, particularly a photo-multiplier, is very low. Therefore, it is required that an extremely strong pulse light, whose photon energy is larger than the bandgaps of IV group semiconductors, is irradiated on IV group semiconductors to measure carrier lifetime correctly. Moreover, it is required that the pulse interval is sufficiently longer than the carrier life-time of IV group semiconductors. Since the conventional light sources, which were used in the carrier lifetime measurement for compound semiconductors, did not satisfy the above-mentioned conditions, this type of measuring method was not able to measure the carrier lifetime of IV group semiconductors.

SUMMARY OF THE INVENTION

A first object of the present invention is to provide a method for measuring a carrier lifetime of IV group semiconductors. A method for measuring a carrier lifetime for IV group semiconductors comprises the steps of irradiating pulse light, whose photon energy is larger than the bandgap of a IV group semiconductor and whose interval is sufficiently longer than the carrier lifetime of a IV group semiconductor, on a IV group semiconductor, exciting said IV group semiconductor, and generating excess carriers; obtaining decay time of a band emission for said IV group semiconductor; and determining a carrier lifetime of said IV group semiconductor from, the decay time of said band emission. It is desirable that the pulse interval is 10 ms or more because excess carriers completely diminish before the next pulse comes. It is also desirable that the energy per one pulse ranges from 5 μJ to 5 mJ in order to create sufficiently large numbers of excess carriers without damaging the IV group semiconductor.

A second object of the present invention is to provide a carrier lifetime measuring apparatus, which is especially appropriate for the carrier lifetime measurement of IV group semiconductors. An apparatus for measuring a carrier lifetime of IV group semiconductors comprises: a light source for generating pulse light whose photon energy is larger than the bandgap of a IV group semiconductor and whose interval is sufficiently longer than the carrier lifetime of a IV group semiconductor; introducing means for introducing said pulse light into said IV group semiconductor; detecting means for detecting band emission emitted from said IV group semiconductor excited by said pulse light; and evaluating means for evaluating the carrier lifetime of said IV group semiconductor from the output of said detecting means.

The above light source is preferable composed of a dye laser and a nitrogen laser or a dye laser and second harmonic generation of a YAG laser. Both a nitrogen laser and second harmonic generation of a YAG laser are employed to excited dye laser. The energy per one pulse of a dye laser preferably ranges 5 $\mu$J to 5 mJ, and that of a nitrogen laser or second harmonic generation of a YAG laser is such that the energy per one pulse of a dye laser ranges from 5 $\mu$J to 5 mJ. The above detecting means is preferably composed of a photo-multiplier having a comparatively high sensitivity for an infrared light region (so-called $S_1$ type). It is desirable that the output of the above detecting means is amplified by a pre-amplifier and averaged by a boxcar averager, and introduced into evaluating means.

According to the above-structured apparatus, the photon energy of the pulse light can be larger than the bandgap of a IV group semiconductor and the pulse interval can be sufficiently longer than the carrier lifetime of a IV group semiconductor. Furthermore, the weak band emission can be measured because a $S_1$ type photo-multiplier has a comparatively high sensitivity for that wavelength region. Additionally, a signal having a sufficiently good S/N ratio can be obtained and a correct measurement can be performed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description give above and the detailed description of the preferred embodiments given below, serve to explain the principles of the invention.

FIG. 2A to 2E are output waveform views at five points A, B, C, D and E shown by broken lines in FIG. 1.

DETAILED DESCRIPTION OF THE PREFERRED EMBODIMENT

Figure 1:
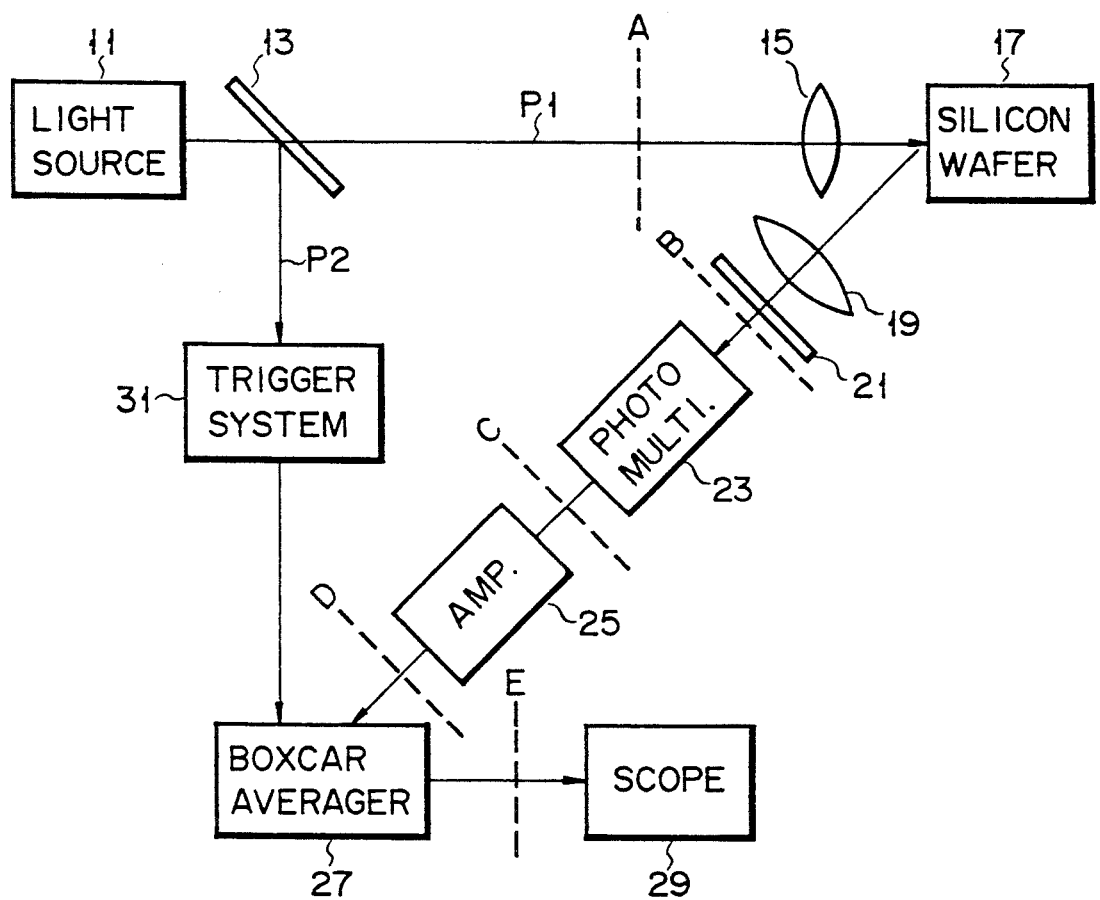
FIG. 1 is a schematic view of a carrier lifetime measuring apparatus according to one embodiment of the present invention.

The present invention will be explained with reference to the drawings. FIG. 1 is a schematic view of a carrier lifetime measuring apparatus according to one embodiment of the present invention. An excitation light source 11 comprises a nitrogen laser and a dye laser. The wavelength of pulse light from a nitrogen laser is 337 nm. The energy per one pulse and the interval of pulse light is 1.3 mJ and 100 ms. Rhodamin 590, whose response time is 1 ns or less, is employed as a dye laser. The dye laser is excited by a nitrogen laser. The dye laser emits a pulse light having a wavelength of 590 nm and an energy of 150 $\mu$J per one pulse. The maximum energy of the nitrogen laser, which is on the market, appears to be about 1.3 mJ at a repeated pulse condition of 10 Hz. If the dye laser is excited by the nitrogen laser having the above maximum energy, the maximum energy of the dye laser is about 150 $\mu$J.

The pulse light emitted from the light source 11 is separated into two directions by a half mirror 13, and is introduced into a condenser lens 15 and a trigger system 31.

As shown in FIG. 2A, the peak power, pulse width and pulse interval of pulse light P1 are 300 kW, 500 ps and 100 ms, respectively. The photon energy of the pulse light is larger than the bandgap energy of a p-type silicon wafer 17 serving as a sample. The carrier lifetime of silicon is much larger than he rise/fall time of a dye laser and much shorter than the pulse interval, which confirms the correct measurement.

Though it is described before that the photon energy should be larger than the bandgap energy of a silicon wafer 17, it is expressed differently that the photon energy is preferably a little larger than the bandgap energy. If the photon energy is much larger than the bandgap energy, the pulse light cannot penetrate deeply into the silicon wafer 17. In that condition, the carrier lifetime cannot be correctly measured because of the influence of the surface recombination.

Pulse light $P_1$ is irradiated on the silicon wafer 17 after passing through the condenser lens 15. The acceptor concentration of the silicon wafer 17 is $10^{18}$ cm$^{-3}$. The beam diameter of pulse light $P_1$, which is about 1 mm before passing through the condenser lens 15, becomes about 100 $\mu$m, after passing through the condenser lens 15.

In the silicon wafer 17, excess electrons and holes are generated. Since a part of these electrons and holes recombine radiatively, the silicon wafer emits a band emission having a wavelength of about 1.2 $\mu$m and an energy per one pulse of about 7.5 to 25 pJ. The part of the band emission passes through a condenser lens 19 and a filter 21, and is introduced into a $S_1$ type photo-multiplier 23 with a response time of 2 ns. The filter removes reflected light with the wavelength of 590 nm before it enters into the photo-multiplier 23. As shown in FIG. 2B, the band emission to be introduced into the photo-multiplier 23 has such a waveform as the intensity decreases exponentially with elapsed time. The relaxation time and the maximum intensity are 1 $\mu$s and 15 $\mu$W, respectively.

A $S_1$ type photo-multiplier has comparatively good sensitivity to the band emission with the peak wavelength of about 1.2 $\mu$m at room temperature. The anode sensitivity of the photo-mutiplier 23 is 4.8A/W to the light with the wavelength of 1.2 $\mu$m. Therefore, the maximum output voltage of the photo-multiplier ranges from 1.8 to 6 mV if a 50 $\Omega$ resistance is employed in the output terminal of the photo-multiplier. The output waveform of the photo-multiplier, which is obtained by introducing the band emission in FIG. 2B into the photomultiplier 23, is shown in FIG. 2C.

The output of the photo-multiplier 23 is introduced into a pre-amplifier 25 having a gain of 20dB and a response time of 1 ns or less, and is amplified to such a level that the maximum voltage ranges from 180 to 600 mV. The output waveform, which is obtained by introducing the signal in FIG. 2C into the pre-amplifier 25, is shown in FIG. 2D. The output of the photo-mutiplier 23 is amplified by 100 times, although the noise is also amplified by more than 100 times at the same time, resulting in the deterioration of S/N ratio.

Thereafter, the output of the pre-amplifier 25 is introduced into a boxcar averager 27 having a response time of 1 ns or less, and is integrated by 3000 times, resulting in an improvement of the S/N ratio. When the output waveform shown in FIG. 2D is introduced into the boxcar averager 27, a sufficiently clear output waveform can be obtained as shown in FIG. 2E. The boxcar averager 27 is controlled by a trigger system 31, into which another pulse light $P_2$ divided by a half mirror 13 is introduced.

The output of the boxcar averager 27 is introduced into an oscilloscope 29. Then, a time interval, during which the maximum output of the boxcar averager 27 reduces to its 1/e, is obtained from the screen of the oscilloscope 29, and the obtained time interval is regarded as a carrier lifetime. Therefore, it is obvious from FIG. 2E that the carrier lifetime of p-type silicon wafer 17 having an acceptor concentration of $10^{18}$ $cm^{-3}$ is about 1 $\mu s$. Additionally, response time of a dye laser, pre-amplifier 25, and boxcar averager 27 are all 1 ns or less, and the response time of the photo-mutiplier 23 is 2 ns or less. Therefore, even the very short carrier of lifetime about 10 ns can be measured.

The present invention is not limited to the above-mentioned embodiment. For example, the above embodiment explained the case of a silicon IV group semiconductor. However, the present invention can be applied to the whole IV group semiconductor, such as germanium and mixed crystals of silicon and germanium.

Only the carrier lifetime in the low level injection can be measured in the above embodiment because acceptor concentration of silicon wafer 17 is as high as $10^{18}$ $cm^{-3}$. However, the carrier lifetime in both low level and high level injection conditions can be obtained if the acceptor concentration of silicon wafer 17 is eg $10^{14}$ $cm^{-3}$ or less.

Pulse light whose energy per one pulse is 150 $\mu J$ to 500 $\mu J$ is irradiated on the silicon wafer 17. If carrier lifetime is assumed to be 1 $\mu s$, excess carrier concentrations of the irradiated area are on the order of $10^{15}$ to $10^{16}$ $cm^{-3}$. Therefore, the carrier lifetime in the high injection condition is measured in a wafer with an acceptor concentration of $10^{14}$ $cm^{-3}$ or less. If a filter is added between the light source 11 and the silicon wafer 17 to decrease the intensity of pulse light and if the excess carrier concentrations are sufficiently lower than $10^{14}$ $cm^{-3}$, the carrier lifetime in low level injection condition is measured. If the acceptor concentration of the silicon wafer 17 is $10^{17}$ $cm^{-3}$ or more, only the carrier lifetime in the low level injection condition can be measured. The present invention can be applied to all the silicon wafer whose carrier concentrations ranges from $10^{13}$ to $10^{20}$ $cm^{-3}$. Additionally, the above-mentioned issues can be also applied to the n-type silicon wafer 17.

In the above embodiment, the carrier lifetime is obtained by introducing the output of the boxcar averager 27 into the oscilloscope. However, the carrier lifetime can be also obtained by introducing the output of the boxcar averager into a computer or into an X-Y recorder.

The above embodiment explained the case of obtaining the carrier lifetime at one point in a silicon wafer 17. However, it is also possible to obtain a carrier lifetime distribution in a silicon wafer 17 by measuring the carrier lifetime at many positions and by introducing the data into a computer.

The above embodiment explained the case in which a nitrogen laser was used as an excitation source of a dye laser. Even if a strong pulse light, such as second harmonic generation of YAG laser, is used instead of a nitrogen laser, the same effect as that of a nitrogen laser can be obtained. The maximum energy per one pulse of a YAG laser, which is on the market for experimental use, is about 100 mJ at a repeated pulse condition of 5 Hz. If a dye laser is excited by the second harmonic generation of a YAG laser having the maximum energy, the maximum energy of a dye laser is of the order of 500 $\mu J$.

The above embodiment explained the case in which the raw wafer is used as a sample. The present invention can be applied to the samples, such as a wafer in processing, a diode, a transistor and a thyristor. According to the present invention, the carrier lifetime change during the device fabrication processes can be detected since it is possible to measure the carrier lifetime in each stage from a raw wafer to a device. In other words, the process check can be performed by using the present invention.

Moreover, the profile of the carrier lifetime towards the vertical direction can be obtained by angle-lapping the raw wafer, the wafer in processing, the diode, the transistor and the thyristor and by measuring the carrier lifetime for those samples. For example, if angle-lapping of 1.2 degrees (about 50 times) is performed to a silicon wafer 17, the profile of the carrier lifetime having an accuracy of 2 $\mu m$ towards the vertical direction can be obtained.

Also, the present invention is not limited to a p-type group semiconductor, and can be applied to a n-type IV group semiconductor.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method for measuring carrier lifetime of IV group semiconductor comprising the steps of:
    generating excess carriers in a IV group semiconductor to be measured, by irradiating pulse light, whose photon energy is larger than the bandgap of said IV group semiconductor and whose interval is sufficiently longer than the carrier lifetime of said IV group semiconductor;
    measuring a time that intensity of band emission of said IV group semiconductor reduces to 1/e of its initial intensity; and
    determining a carrier lifetime of said IV group semiconductor from said time.

2. The method according to claim 1, wherein said interval of said pulse light is 10 ms or more and the energy per one pulse ranges from 5 $\mu J$ to 5 mJ.

3. The method according to claim 1, wherein said pulse light is emitted from a dye laser excited by a nitrogen laser or second harmonics generation of a YAG laser.

4. The method according to claim 3, wherein the energy per one pulse of said nitrogen laser is such that the energy per one pulse said dye laser ranges from 5 $\mu J$ to 5 mJ.

5. The method according to claim 1, wherein said pulse light is emitted from a dye laser excited by second harmonics generation of a YAG laser.

6. The method according to claim 5, wherein said energy per one pulse from said second harmonics generation of said YAG laser is such that type energy per one pulse of said dye laser ranges from 5 $\mu J$ to 5 mJ.

7. The method according to claim 1, wherein said step for measuring a time that intensity of band emission of said IV group semiconductor reduces to 1/e of its initial intensity comprise the steps of: amplifying said band emission; and averaging said amplified band emission.

8. The method according to claim 1, wherein said step for determining said carrier lifetime is performed by using oscilloscope.

9. An apparatus for measuring carrier lifetime of IV group semiconductor comprising:
   a light source for generating pulse light whose photon energy is larger than the bandgap of said IV group semiconductor and whose interval is longer then the carrier lifetime of said IV group semiconductor;
   introducing means for introducing said pulse light into said IV group semiconductor;
   detecting means for detecting band emission emitted from said IV group semiconductor excited by said pulse light; and
   evaluating means for evaluating the carrier life of said IV group semiconductor from the output of said detecting means.

10. The apparatus according to claim 9, wherein said light source generates pulse light wherein said interval of said pulse light is 10 ms or more and the energy per one pulse ranges from 5 $\mu J$ to 5 mJ.

11. The apparatus according to claim 9, wherein said light source is composed of a dye laser and a nitrogen laser exciting the dye laser.

12. The apparatus according to claim 11, wherein the energy per one pulse of the dye laser ranges from 5 $\mu m$ to 5 mJ.

13. The apparatus according to claim 9, wherein said light source is composed of a dye laser and second harmonic generation of a YAG laser exciting the dye laser.

14. The apparatus according to claim 13, wherein said dye laser is excited by a second harmonic generation of said YAG laser.

15. The apparatus according to claim 9, wherein said detecting means is composed of a photo-multiplier having good sensitivity for a infrared wavelength region (so-called $S_1$ type).

16. The apparatus according to claim 9, wherein said evaluating means is composed of an oscilloscope.

17. The apparatus according to claim 9, wherein the output of said detecting means is amplified by amplifying means and averaged by averaging means, and introduced into said evaluating means.

18. The apparatus according to claim 17, wherein said averaging means is composed of a boxcar averager.

* * * * *